(12) United States Patent
Pienkos et al.

(10) Patent No.: US 7,557,181 B2
(45) Date of Patent: *Jul. 7, 2009

(54) PAN-HER ANTAGONISTS AND METHODS OF USE

(75) Inventors: Philip T. Pienkos, The Woodlands, TX (US); Daniel J. Monticello, The Woodlands, TX (US)

(73) Assignee: Molecular Logix, Inc., The Woodlands, TX (US)

( * ) Notice: Subject to any disclaimer, the term of this patent is extended or adjusted under 35 U.S.C. 154(b) by 294 days.

This patent is subject to a terminal disclaimer.

(21) Appl. No.: 11/172,611

(22) Filed: Jun. 30, 2005

(65) Prior Publication Data

US 2006/0154333 A1 Jul. 13, 2006

Related U.S. Application Data

(60) Provisional application No. 60/643,089, filed on Jan. 11, 2005.

(51) Int. Cl.
*C07K 14/475* (2006.01)
*C07K 14/485* (2006.01)

(52) U.S. Cl. .................. 530/300; 530/388.24; 530/399

(58) Field of Classification Search .................. None
See application file for complete search history.

(56) References Cited

U.S. PATENT DOCUMENTS

| 5,102,789 | A | 4/1992 | Siegel et al. |
| 2005/0032162 | A1 | 2/2005 | Coco et al. |

OTHER PUBLICATIONS

Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Rajput et al. Cancer Res. 2007; 67: 665-673.*
Kolesta et al. Neoplasia. 2008; 10: 687-96.*
U.S. Appl. No. 11/172,610, filed Jun. 30, 2005, Jeffrey S. Bishop, et al.
Wells, James A., "Additivity of Mutational Effects in Proteins," *Biochemistry*, 29 (37): 8509-8517 (1990).
Bowie, James U., "Deciphering the Message in Protein Sequences: Tolerance to Amino Acid Substitutions," *Science*, 247: 1306-1310 (1990).
Coco, Wayne M., et al., "Growth Factor Engineering by Degenerate Homoduplex Gene Family Recombination," *Nature Biotechnology*, 20: 1246-1250 (2002).

* cited by examiner

*Primary Examiner*—Christina Borgeest
(74) *Attorney, Agent, or Firm*—Elmore Patent Law Group, P.C.; Darlene A. Vanstone; Carolyn S. Elmore (57) ABSTRACT

The present invention features human epidermal receptor (HER) antagonists. These antagonists are polypeptide variants of ligands of HER. The HER ligand polypeptide variants of the invention possess Pan-HER antagonistic properties and can inhibit at least one HER-mediated biological activity of one or more HER subtypes, such as inhibition of the receptor's kinase activation activity and subsequently, cell proliferation. Such polypeptide variants, and nucleic acids encoding these polypeptide variants can be used therapeutically in situations in which inhibition of HER activity is indicated.

24 Claims, 6 Drawing Sheets

```
NSDSECPLSHDGYCLHDGVCMYIEALD---KYACNCVVGYIGERCQYRDLKWWELR      EGF    SEQ. ID#9
SHLVKCAEKEKTFCVNGGECFMVKDLSNPSRYLCKCPNEFTGDRCQNYVMASF         HRGβ   SEQ. ID#10
SHLVKCPLSHDGYCLHDGVCMYIEALD---KYACNCVVGYIGERCQYRDLKWWELR      BiR    SEQ. ID#11
```

G39L +Amp ds

FIG. 5A

G39L +BTC ds

FIG. 5B

G39L +Epi ds

FIG. 5C

G39L +TGF-α ds

FIG. 5D

PAN-HER ANTAGONISTS AND METHODS OF USE

RELATED APPLICATION

This application claims the benefit of U.S. Provisional Application No. 60/643,089, filed on Jan. 11, 2005. The entire teachings of the above application are incorporated herein by reference.

GOVERNMENT SUPPORT

The invention was supported, in whole, or in part, by National Cancer Institute Grant Number R43 CA095930-02. The Government has certain rights in the invention.

BACKGROUND OF THE INVENTION

Epidermal growth factor (EGF) is a 53 amino acid cytokine which is proteolytically cleaved from a large integral membrane protein precursor. EGF plays an important role in the growth control of mammalian cells. The amino acid and nucleotide sequences of human EGF (EGF) are, for example, disclosed in Hollenberg, "Epidermal Growth Factor-Urogastrone, A Polypeptide Acquiring Hormonal States"; eds., Academic Press, Inc., New York (1979), pp. 69-110; or Urdea et al., Proc. Natl. Acad. Sci. USA. 80, 7461 (1983). The amino acid sequence of EGF is also disclosed in U.S. Pat. No. 5,102,789 and copending U.S. patent application Ser. No. 10/820,640 both of which are incorporated herein by reference in their entirety.

Human Epidermal Receptors (HER), including epidermal growth factor receptors (EGFR), are well known example of receptor tyrosine kinases. Interaction of HERs with their cognate ligands, or with structurally related ligands, leads to dimerization and activation of the kinase domain. This initiates a signaling cascade, leading to cell division. Overexpression of the genes coding for HER family members has been implicated in a number of cancers including breast, ovarian, and head and neck cancer. Molecules that target EGFR (HER1) by inhibiting its kinase activity or by interfering with the binding of EGF to EGFR have been shown to inhibit cell proliferation and have been developed as anticancer therapeutics, for example, Iressa® (gefitinib), a tyrosine kinase inhibitor and Erbitux™ (cetuximab), an EGFR-specific monoclonal antibody. Additional molecules including monoclonal antibodies such as Herceptin target other individual members of the HER family. Recently, several monoclonal antibodies and small molecule kinase inhibitors (e.g. Panituzumab and Lapatnib) have entered development as examples of molecules that target multiple HER receptors. Although these therapeutics have been shown to be effective in some cases, there is still a need for novel therapies for HER-related cancers, particularly a therapeutic compound that interferes with the entire HER family.

SUMMARY OF THE INVENTION

The present invention features novel Pan-HER antagonists. By "Pan-HER antagonist" is meant any molecule that inhibits, suppresses or causes the cessation of multiple HER-mediated biological activity, e.g. by reducing, interfering with, blocking, or otherwise preventing the interaction or binding of a native or active HER ligand to HER, preferably HER1, HER2, HER3, and/or HER4 and variant forms of these receptors. Direct interference with HER1, HER3 and HER4 can provide indirect interference with HER2, by eliminating the dimerization partners required for activity. These Pan-HER antagonists are HER ligand polypeptide variants. Preferred HER ligand variants of the invention are non-naturally occurring polypeptide molecules that are capable of blocking or interrupting at least one biological activity of HER family members, for example, reducing or inhibiting HER kinase activation, signaling, regulation, dimerization, or HER-regulated cell proliferation. Preferred ligand variants of the invention are variants capable of selectively inhibiting at least one HER-mediated biological activity. Such HER ligand polypeptide variants, and nucleic acids encoding these polypeptide variants, can be used therapeutically in situations in which inhibition of HER biological activity is indicated, e.g. cancer. The term "polypeptide" is used herein as a generic term to refer to native protein, fragments, homologs or analogs of a relevant polypeptide sequence.

In one aspect, the present invention features a HER ligand variant derived from a naturally occurring HER ligand that has at least one amino acid substitution at the glycine of position 39 (G39 or Gly 39) corresponding to wild type EGF Gly 39, and having at least one domain from another, different, HER ligand a ("substituted domain") and having at least one Pan-HER antagonist activity. In a preferred embodiment, glycine is preferably substituted with leucine (G39L) at the position corresponding to wild type EGF Gly 39, and the substituted domain is preferably the amino terminal domain of EGF.

The present invention also features a method of treating a condition characterized by HER over-expression in a patient, comprising administering to the patient a therapeutically effective amount of a pharmaceutical composition comprising at least one HER polypeptide variant of the invention.

DETAILED DESCRIPTION OF THE INVENTION

The present invention features novel Pan-HER antagonists. These Pan-HER antagonists are HER ligand polypeptide variants. Examples of HER ligands include mammalian EGF (e.g. human (EGF), pig, cat, dog, mouse, horse and rat). Other examples of HER ligands include transforming growth factor-α (TGFα), betacellulin, heparin-binding EGF-like growth factor (HB-EGF), neuregulins, heregulin (HRG) including HRGα, HRGβ1, HRGβ2 and HRG-factor (NDF), amphiregulin (AR) and epiregulin. Preferred HER ligand variants of the invention are based on human HER ligand polypeptide variants capable of selectively inhibiting HER-mediated biological activity.

The present invention is based on the inventor's previous discovery that EGF that has been modified to substitute the glycine of position 39 with another amino acid, preferably leucine (referred to herein as "EGF G39L"), causes EGF to become an EGFR (HER1) antagonist (see the U.S. Utility application Ser. No. 11/172,610 entitled "Epidermal Growth Factor Receptor Antagonists and Methods of Use," filed on Jun. 30, 2005, incorporated herein by reference). The inventors have now discovered that by "swapping" the structural domains of other HER family ligands into EGF G39L, new HER ligand chimeric molecules result that maintain the antagonist activity of EGF G39L and further provide added versatility by allowing additional HER molecules to be targeted for inhibition by the same HER ligand variant. A single HER ligand-variant specific for HER1, HER3 and HER4 is very desirable as it provides a powerful therapeutic for targeting multiple cancers in which undesirable HER-mediated biological activity of one or more HER family members is implicated.

Considering the significant structural similarities of the receptors and the HER ligands, it is believed that the G39 residue or that amino acids corresponding to the G39 residue in other HER ligands plays the same role throughout the HER ligand family and therefore, it is believed that any HER ligand having a G39L substitution or the equivalent thereof can serve as the starting point for designing a HER ligand polypeptide variant (e.g. a chimera) of the invention.

In one aspect, the present invention features HER ligand polypeptide variants derived from a naturally occurring HER ligand that has at least one amino acid substitution at the glycine of position 39 (G39 or Gly 39) corresponding to wild type EGF Gly 39, and having at least one domain from another, different, HER ligand (a "substituted domain") and having at least one Pan-HER antagonist activity. In this embodiment, the ligand is characterized by a disrupted binding by Domain III but binds its receptor by Domain I. In a preferred embodiment, glycine is preferably substituted with leucine (G39L) at the position corresponding to wild-type EGF Gly 39, and the substituted domain is the amino terminal domain of EGF. As used herein, the phrase "the amino acid position that corresponds to amino acid G39 of wild-type human EGF" means that when the unmodified HER ligand from various mammalian species is aligned with human wild-type EGF for optimal comparison, the glycine that appears at or near the positions that correspond to G39 of human wild-type EGF is aligned (see the U.S. Utility application Ser. No. 11/172,160 entitled "Epidermal Growth Factor Receptor Antagonists and Methods of Use," filed on Jun. 30, 2005, incorporated herein by reference).

Figure 1:
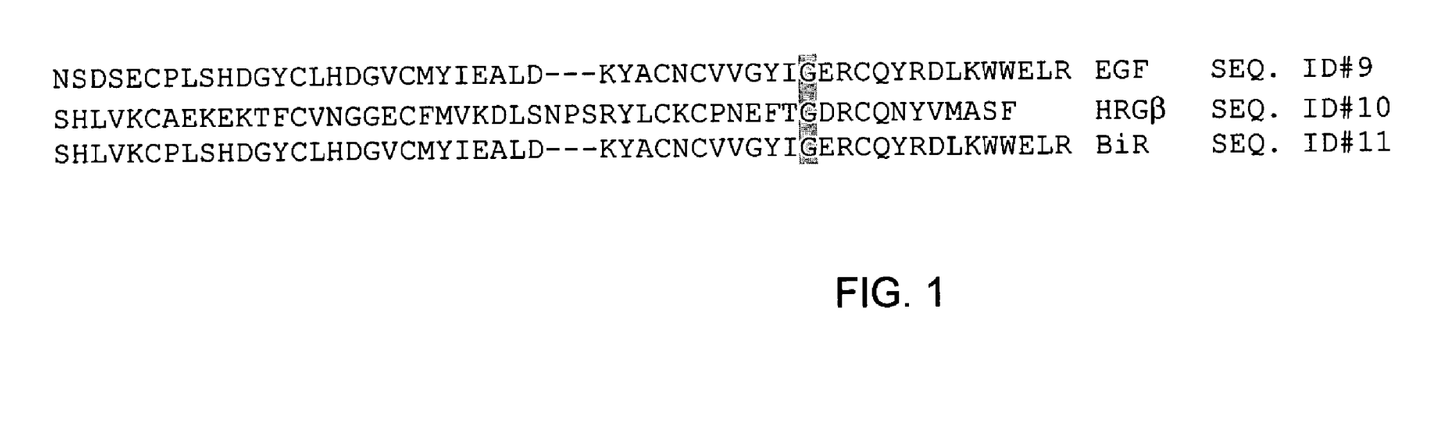
FIG. 1 shows the sequence alignment of EGF, HRGβ1 and BiR.

In another aspect, the present invention features a synthetic HER ligand polypeptide variant such as the synthetic heregulin/EGF chimera known as BiRegulin (FIG. 1) that has at least one amino acid substitution at the glycine of position 39 corresponding to wild type EGF Gly 39. BiRegulin (BiR) is a chimeric EGF homolog, in which the amino terminal residues (NSDSE) of EGF, have been replaced with the corresponding residues of HRGβ1 (SHLVK).

In yet another aspect, the invention features a synthetic ligand polypeptide variant wherein the binding of one of Domain I or III is disrupted while maintaining or increasing the binding to the other of Domain I or III. These variants can be made by modifying other amino acids (e.g., R41D) in Domain I and/or III as those variants exemplified herein. These variants can advantageously be modified or engineered to alter the native receptor specificity (either broaden the specificity such that the variant binds to additional receptors or target specificity towards a specific receptor). This can be done either by additional mutations or the domain swapping strategies discussed herein.

By "HER-mediated biological activity" as used herein is meant the intrinsic protein-tyrosine kinase activity of HER and its downstream signal transduction cascade which ultimately leads to DNA synthesis and cell proliferation.

By "Pan-HER antagonist" is meant any molecule that inhibits, suppresses or causes the cessation of HER-mediated biological activity, e.g. by reducing, interfering with, blocking, or otherwise preventing the interaction or binding of a native or active HER ligand to one or more subtypes of HER. The use of the term "antagonist" is used herein in a functional sense and is not intended to limit the invention to compounds having a particular mechanism of action. For example, the term "antagonist" includes, but is not limited to, a molecule that functions as a competitive antagonist. A competitive antagonist binds the HER receptor but does not trigger the biological activity of HER.

Ligand polypeptide variants of the invention (including "HER ligand chimerae") possess a number of useful properties. For example, the polypeptide variants of the present invention can be used to treat diseases wherein overexpression of HER is implicated in the pathological process of the disease (e.g. cancer).

In accordance with the invention, G39 may be substituted with any suitable amino acid such that the Pan-HER antagonistic activity of the modified HER ligand polypeptide remains intact. For example, G39 can be replaced by glutamate (G39E), glutamine (G39Q), lysine (G39K), aspartic acid (G39D), isoleucine (G39I), or leucine (G39L). In a particularly preferred embodiment G39 is replaced by phenylalanine (G39F), leucine (G39L), aspartic acid (G39D), or isoleucine (G39I). G39L is preferred.

In addition to the G39 amino acid modification, HER polypeptide variants of the invention comprise a substituted domain, from another, different, HER ligand. In a preferred embodiment, the substituted domain is all or a portion of the residues SHLVK, taken from HRGβ-1 and substituted for the comparable residues in EGF, preferably some portion of amino acids 1-5 of the amino terminus of EGF corresponding to amino acids NSDSE. In a preferred embodiment of the invention, the HER polypeptide variant is BiRegulin (BiR) having at least one amino acid substitution at the glycine of position 39 corresponding to wild type EGF, wherein the glycine of position 39 corresponding to wild type EGF Gly 39 or G39 has been replaced by leucine (BiRG39L) or another suitable amino acid. In another preferred embodiment BiRG39L is further substituted at amino acid position 35 wherein the amino acid valine at that position is replaced with the amino acid glutamate (BiRV35EG39L). Such HER polypeptide variants of the invention also possess at least one Pan-HER antagonist activity and are preferably capable of antagonizing each of the HER subtypes, HER1, HER3 and HER 4.

As is known in the art, the ligands that bind HER receptors can be grouped into three categories: 1) Those that bind to HER1 alone (EGF, TGF-a, amphiregulin), 2) those that bind to HER3 and/or HER4 (heregulins and neuregulins) and 3) those that bind to HER-1 and HER-4 (betacellulin, heparin-binding EGF, NRG3, epiregulin) (Riese and Stern 1998 Bioessays 20:41). Each HER receptor exists as a monomer in the inactive state. Ligand binding promotes either homodimerization or heterodimerization between the bound receptor and other members of the HER family. The various EGF-like growth factors bind with high affinity to each ErbB receptor except HER2, which has no known ligand and has the constitutive ability to form homodimers and heterodimers. Homodimers are not generally implicated in tumor cell growth, but are important for cardiac muscle development and repair. (Dougall et al 1994 Oncogene 9:2109, Hynes and Stern 1994, Biochim Biophys Acta 1198:165, Tzahar and Yarden 1998 Biochim Biophys Acta 1377:M25, Negro et al 2004, Recent Prog Horm Res. 59:1.). HER2 is the preferred heterodimeric partner of the other HER receptors (Tzahar et al 1996, Mol Cell Biol 16:5276, Beerli et al 1995 Mol Cell Biol 15:6496, Karunagaran et al 1996 EMBO J 15:254, Wang et al 1998, PNAS95:6809). HER3 differs from the other HER family members in that it has a deficient tyrosine kinase domain (Guy et al 1994 PNAS 91:8132) and must associate with another HER-family receptor to trigger signaling.

The advantage of the HER polypeptide-variants of the invention such as BiRG39L or BiRV35EG39L is that they are specific for multiple HER targets such as HER1, HER3 and HER4 and can antagonize each of these HER subtypes. It is not necessary that the variant of the invention target HER2, because the targeting of HER1, HER3 and HER4 by the variants of the invention effectively eliminates all HER2 heterodimerization partners thereby suppressing HER2 biological activity that may be undesirable. It is advantageous to avoid suppression of HER2 homodimerization because such activity has been shown to cause cardiomyopathy, a life threatening side effect.

Other "domain swaps" can be envisioned as well and are included in the present invention. For example the B-loop of EGF that corresponds to amino acids 21-30 of mature EGF may be substituted with a corresponding B-loop domain of another, different, preferably human, HER ligand, such as human transforming growth factor-α (TGFα), betacellulin, heparin-binding EGF-like growth factor (HB-EGF), neuregulins, heregulin (HRG), amphiregulin (AR) and epiregulin. The corresponding B-loop domain can be incorporated to alter the HER specificity of the antagonist. Thus, where EGF G39L is the starting point for designing a HER ligand polypeptide of the invention, the B-loop of EGF G39L is substituted with the corresponding domain of a B-loop of a different HER ligand that is known to interact with the specific HER molecule that is intended to be antagonized. Such modified chimeras can possess the antagonist activities of the EGF G39L variant with altered binding specificity based on the source of the B-loop swap.

Therefore, to design a Pan-HER ligand polypeptide variant of the invention with enhanced targeting of HER1, the EGF B-loop domain may be substituted with the corresponding B-loop domain from TGF-alpha, or amphiregulin. To design a pan-HER ligand polypeptide of the invention with enhanced targeting of HER3 and/or HER4, the EGF B-loop domain may be substituted with the corresponding domain from the neuregulins. Pan-HER ligand polypeptide variants with enhanced targeting of HER1 and HER4, may substitute the EGF B-loop domain with the corresponding domain from betacellulin, HB-EGF, NRG3 or epiregulin. As HER2 has no known ligand, it can be indirectly targeted for downregulation by eliminating the HER1, HER2, or HER4 dimerization partners required for activity, that is, by antagonizing HER1, HER 3 and HER4 using the polypeptide variants of the invention. Examples of antagonistic properties of B-loop swaps are shown in FIGS. 5A-5D In addition, homologs, analogs and fragments of the HER ligand polypeptide variants are within the scope of the present invention. By "homologs" is meant the corresponding polypeptides of HER ligands from other mammalian species having substantial identity to human wild-type HER ligands, so long as such homologs retain Pan-HER antagonist activity. For example, homologs of EGF polypeptide sequences for various mammalian species are as follows:

```
NSDSECPLSHDGYCLHDGVCMYIEALDKYACNCVVGYIGERCQYRDLKWWELR  Human  (SEQ ID NO:1)
NSYSECPPSHDGYCLHGGVCMYIEAVDSYACNCVFGYVGERCQHRDLKWWELR  Pig    (SEQ ID NO:2)
NSYQECPPSYDGYCLYNGVCMYIEAVDRYACNCVFGYVGERCQHRDLK-WELR  Cat    (SEQ ID NO:3)
NGYRECPSSYDGYCLYNGVCMYIEAVDRYACNCVFGYVGERCQHRDLK-WELR  Dog    (SEQ ID NO:4)
NSYPGCPSSYDGYCLNGGVCMHIESLDSYTCNCVIGYSGDRCQTRDLRWWELR  Mouse  (SEQ ID NO:5)
NSYQECSQSYDGYCLHGGKCVYLVQVDTHACNCVVGYVGERCQHQDLR-----  Horse  (SEQ ID NO:6)
NSNTGCPPSYDGYCLNGGVCMYVESVDRYVCNCVIGYIGERCQHRDLRWWKLR; Rat    (SEQ ID NO:7)
```

"Analogs" is meant to include polypeptide variants which differ by one or more amino acid alterations, e.g., substitutions, additions or deletions of amino acid residues that still maintain the EGFR antagonistic properties of the relevant peptides.

Besides the mutations at position G39 of EGF or at the amino acid position that corresponds to amino acid G39 of wild-type human EGF in other Pan-HER ligands, additional mutations are possible which will leave the Pan-HER inhibitory activity or antagonist activity of the Pan-HER ligand polypeptide variants substantially intact. These mutations may take the form of single or multiple substitutions, deletions, or insertions. Amino acid substitutions may take the form of conservative or non-conservative amino acid substitutions at one or more locations on the polypeptide. As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

The therapeutic qualities of the HER ligand polypeptide variants of the invention may also be further improved through amino acid substitutions, deletions and insertions at locations in addition, or as an alternative, to G39. These improved therapeutic qualities include, but are not limited to, enhanced affinity, increased half-life, increased solubility, and increased bioavailability. In one preferred embodiment, substitutions, deletions or insertions at any combination of positions G18, V35, G39 and/or R41 of BiR or at positions in other HER ligands corresponding to G18, V35, G39 and/or R41 of wild type EGF, are possible when designing a HER ligand chimera of the invention. It is particularly preferred to prepare a variant that has disrupted binding via one of the binding domains (Domain I or III) while increasing binding (enhancing affinity) via the other binding domain. A preferred HER ligand variant of the invention is BiRV35EG39L.

HER ligand polypeptide variants in accordance with the present invention can be designed, made and tested using any number of methods. Domain swapping, amino acid substitutions, deletions or insertions can be accomplished by methods known in the art such as site directed mutagenesis. The resulting mutated polypeptides are then tested for Pan-HER antagonistic activity using in vitro screening assays such as those described herein or any other suitable screening assay.

The data described herein and shown in FIGS. 5A-D indicates that HER ligand polypeptide variants based on EGF having amino acid substitutions at G39 and having a substituted domain from another, different HER ligand such as amphiregulin, betacellulin, epiregulin and TGF alpha, inhibit the proliferation of cells. The inhibitory or Pan-HER antagonistic activity of a candidate polypeptide of the invention can further be assessed by any other suitable assay or other method, and compared to HER activity in the presence of wild-type human ligand polypeptide.

As described above, the polypeptide variants of the present invention, their homologs and analogs have substantial identity to wild-type ligand. As used herein, "substantial identity" means at least 60% sequence identity, preferably at least 70% identity, preferably at least 80% and more preferably at least 90% sequence identity to the amino acid sequence of wild-type human ligand (or domains thereof in the instance where the variant is a chimera produced by swapping domains), while maintaining HER inhibitory or other Pan-HER antagonist activity. In other embodiments, the polypeptide variants of the present invention have at least 91%, at least 92%, at least 93%, at least 94%, at least 95% at least 96%, at least 97%, or at least 98% amino acid identity to the amino acid sequence of wild-type human ligand, while maintaining HER inhibitory or other Pan-HER antagonist activity. The percent identity of two nucleotide or amino acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions×100). The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA*, 90:5873-5877 (1993). Such an algorithm is incorporated into the BLASTN and BLASTX programs (version 2.2) as described in Schaffer et al., *Nucleic Acids Res.* 29:2994-3005 (2001).

The polypeptide variants of the invention may be produced by several techniques. In one preferred embodiment, the polypeptide variants of the invention are produced by expression in a suitable host of a gene coding for the relevant polypeptide variant. Such a gene is most readily prepared by site-directed mutagenesis of wild-type human gene as described herein. However, the polypeptide variants of the invention may be produced in whole or in part by chemical synthetic techniques such as by a Merrifield-type synthesis. Chemical synthesis of all or a portion of a modified polypeptide of the invention may be particularly desirable in the case of the use of a non-naturally occurring amino acid substituent in the polypeptide variant.

The present invention also provides nucleic acid molecules encoding a HER ligand polypeptide of the invention. The nucleic acid molecules of the present invention can be RNA, for example, mRNA, or DNA. DNA molecules can be double-stranded or single-stranded. The nucleic acid molecule can also be fused to a marker sequence, for example, a sequence that encodes a polypeptide to assist in isolation or purification of the polypeptide. Such sequences include, but are not limited to, those that encode a glutathione-S-transferase (GST) fusion protein, those that encode a hemagglutinin A (HA) polypeptide marker from influenza, and sequences encoding a His tag.

It will be appreciated by those skilled in the art that the design of the expression vector can depend on such factors as the choice of the host cell to be transformed and the level of expression of polypeptide desired. The expression vectors of the invention can be introduced into host cells to thereby produce the modified polypeptides of the invention, including fusion polypeptides, encoded by nucleic acid molecules as described herein. Molecular biology techniques for carrying out recombinant production of the modified polypeptides of the invention are well known in the art and are described for example, in, Sambrook, et al., *Molecular Cloning: A Laboratory Manual* (Cold Spring Harbor Lab Press); $3^{rd}$ ed., 2000).

The present invention also pertains to pharmaceutical compositions comprising the HER ligand polypeptide variants described herein. For instance, a polypeptide variant of the invention can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylase or starch, dextrose, magnesium stearate, talc, silicic acid, viscous paraffin, perfume oil, fatty acid esters, hydroxymethylcellulose, polyvinyl pyrrolidone, etc., as well as combinations thereof. In addition, carriers such as liposomes and microemulsions may be used. The polypeptide variants of the invention may also be covalently attached to a protein carrier such as albumin, or a polymer, such as polyethylene glycol so as to minimize premature clearing of the polypeptides. The pharmaceutical preparations can, if desired, be mixed with auxiliary agents, e.g. lubricants, preservatives, stabilizers, wetting agents, emulsifiers, salts for influencing osmotic pressure, buffers, coloring, flavoring and/or aromatic substances and the like that do not deleteriously react with the active agent in the composition (i.e., a polypeptide and/or nucleic acid molecule of the invention).

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrrolidone, sodium saccharine, cellulose, magnesium carbonate, etc.

Methods of introduction of these compositions include, but are not limited to, transdermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devices ("gene guns") and slow release polymeric devices. The pharmaceutical compositions of this invention can also be administered as part of a combination therapy with other compounds.

The HER ligand polypeptide variants of the present invention can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentration in a hermetically sealed container such as an ampoule or sachette indicating the quantity of active compound (polypeptide and/or nucleic acid). Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

The HER ligand polypeptide variants described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The HER ligand polypeptide variants of the invention are administered in a therapeutically effective amount. The amount of polypeptide that will be therapeutically effective in the treatment of a particular disorder or conditions will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of the disease or condition, and should be decided according to the judgment of a practitioner and each patient's circumstances. Effective doses may be extrapolated from dose-response curves derived from in vitro or animal model test systems.

The present invention also pertains to methods of treatment (prophylactic, diagnostic, and/or therapeutic) for conditions characterized by HER overexpression. A "condition characterized by HER overexpression" is a condition in which the presence of a polypeptide variant of the invention is therapeutic. Such conditions include many types of cancer. For example, many tumors of mesodermal and ectodermal origin overexpress members of the HER family. HER receptors have been shown to be overexpressed in many gliomas, squamous cell carcinomas, breast carcinomas, melanomas, invasive bladder carcinomas and esophageal cancers. In addition, studies with primary human mammary tumors have shown a correlation between high HER gene expression and the presence of metastases, higher rates of proliferation, and shorter patient survival. Overexpression of HER genes has also been implicated in a variety of other disorders such as psoriasis, and fibrosis.

The term "treatment" as used herein, refers not only to ameliorating symptoms associated with the disease or condition, but also preventing or delaying the onset of the disease, and also lessening the severity or frequency of symptoms of the disease or condition. More than one polypeptide variant of the present invention can be used concurrently as a co-therapeutic treatment regimen, if desired. As used herein, a "co-therapeutic treatment regimen" means a treatment regimen wherein two drugs are administered simultaneously, in either separate or combined formulations, or sequentially at different times separated by minutes, hours or days, but in some way act together to provide the desired therapeutic response. The polypeptides of the invention may also be used in conjunction with other drugs that inhibit various aberrant activities of the HER receptor. Such additional drugs include but are not limited to HER-specific antibodies, small molecule kinase inhibitors, and traditional chemotherapeutic agents.

The therapeutic compound(s) of the present invention are administered in a therapeutically effective amount (i.e., an amount that is sufficient to treat the disease or condition, such as by ameliorating symptoms associated with the disease or condition, preventing or delaying the onset of the disease or condition, and/or also lessening the severity or frequency of symptoms of the disease or condition). The amount that will be therapeutically effective in the treatment of a particular individual's disease or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or condition, and should be decided according to the judgment of a practitioner and each patient's circumstances. Effective doses may be extrapolated from dose-response curves derived from in vitro or animal model test systems.

The therapeutic compounds of the present invention can be used either alone or in a pharmaceutical composition as described above. For example, the gene for a modified polypeptide of the present invention, either by itself or included within a vector, can be introduced into cells (either in vitro or in vivo) such that the cells produce the desired polypeptide. If desired, cells that have been transfected with the nucleic acid molecule of the present invention can be introduced (or re-introduced) into an individual affected with the disease.

Other gene transfer systems, including viral and nonviral transfer systems, can be used. Alternatively, nonviral gene transfer methods, such as calcium phosphate co-precipitation, mechanical techniques (e.g., microinjection); electroporation; membrane fusion-mediated transfer via liposomes; or direct DNA uptake, can also be used to introduce the desired nucleic acid molecule into a cell.

EXAMPLES

Example 1

Methods and Materials

Cloning and gene expression. The human epidermal growth factor gene (EGF) was synthesized chemically and ligated into the Pet-9a vector (Novagen) at the NdeI and BamHI cloning sites. The EGF gene contained the OmpA leader sequence followed by an N-terminal 6x-his tag and a factor Xa cleavage site for future his-tag removal, if necessary, and corresponds to the following amino acid sequence:

```
----OmpA leader------ -his-tag- -Xa-- -----------EGF------------------------------
MKKTAIAIAVALAGFATVAQAHHHHHHIEGRNSDSECPLSHDGYCLHDGVCMYIEALDKYACNCWGYIGERCQYRDLKWWELR.     (SEQ ID NO: 8)
```

This original clone, designated pMLPP1, was used as a basis for creating all Pan HER ligand variants (including substitution, deletion, insertion and domain swap variants) using the QuickChange mutagenesis kit (Stratagene). For protein production the EGF plasmids were transformed into *E. coli* strain BL21 (DE3) pLysS (Novagen).

Production of ligand variants. Single colonies were inoculated into shake flask cultures containing 15 ml LB+Km25+Cm30. After growth overnight, samples of culture were frozen for stocks, and for plasmid preps to confirm the identities of the EGF variant gene inserts. The remaining cultures were used to inoculate production cultures in Terrific Broth+Km25+Cm30. Cells were induced with 0.2 mM IPTG during early log phase, and the cultures were grown overnight. Culture supernatants were collected by centrifugation and production was confirmed by dot blot using the Mouse Western Breeze Chromogenic Immunodection System (Invitrogen cat#WB7103) with primary antibody: 1:1000 mouse anti-penta his antibody (Qiagen cat#34660).

EGF protein purification. Three ml of Ni-NTA resin (Qiagen #30230) was used to pack 5 ml columns (Qiagen cat#34964) which were equilibrated with PBS pH 8.0. Culture supernatants were adjusted to pH 7.5-8.0 with 1N HCL before loading on columns. Columns were washed with PBS and PBS+10 mM imidazole; EGF variant proteins were eluted from columns with PBS+250 mM imidazole. Bradford protein assays were used to monitor protein concentrations.

Protein concentrate and buffer exchange. Column eluents were dialyzed in PBS at 4° C. with one buffer exchange, and then concentrated with 3000 MWCO Macrosep centrifuge devices (ISC# OD003C41). The final product was tested for protein concentration using the BCA method and for purity by SDS-PAGE.

Example 2

Cell Proliferation Stimulation Assays

The HER5 cell line, a murine fibroblast line (derived from the NR-6 line) that has been stably transfected to express the human EGF receptor was provided by Dr. M. C. Hung (MD Anderson Cancer Center). Stock cultures of HER5 were propagated in D-MEM/F12 medium containing 10% fetal bovine serum, 100 units/ml of penicillin and 100 ug/ml of streptomycin in a water-jacketed incubator at 37° C. in a humidified 5% $CO_2$ atmosphere. For HER5 proliferation assays, the cells were changed into DMEM/F12 without serum for 24 hours. Cells were then trypsinized and suspended at 1E5 cells/ml. Serial dilutions of EGF (PeproTech, Rocky Hill, N.J.), and HER ligand polypeptide variants were prepared in serum-free DMEM/F12 at 2-fold the final concentration and plated into the wells of 96-well plates. Fifty microliters of cell suspension (5000 cells) were added to appropriate wells bringing the total volume to 100 ul at the desired concentrations. Plates were incubated for a 48 hour proliferation period. Cell proliferation was determined by addition of 10 ul/well of WST-1 Cell Proliferation Reagent (Roche Applied Sciences, Indianapolis, Ind.) for the last three hours of the proliferation period. WST-1 is a tetrazolium salt that is cleaved to formazan dye by mitochondrial dehydrogenases in viable cells. The amount of formazan was measured at 450 nm using a microplate reader (Dynex Technologies) with MRX Revelation software.

MCF-7 cells were obtained from the American Type Culture Collection (ATCC). Stock cultures of MCF-7 were maintained in Eagle's MEM supplemented with 1% ITS-X (Invitrogen) and 10% fetal bovine serum. For proliferation assays, MCF-7 cells were transferred to serum-free medium (SFM) for 24 hours and then trypsinized and suspended at 1E5 cells/mL in SFM. Fifty microliters of cell suspension (5000 cells) were plated per well in 96 well microtiter plates. Serial dilutions of HER ligands or mutant proteins were prepared at twice the final concentration in SFM and 50 ul was added to wells, bringing the final volume to 100 ul at the desired final concentration. Plates were incubated for 72 hours at 37 C in a humidified 5% CO2 atmosphere. Cell proliferation was determined by addition of 10 ul/well of WST-1 Cell Proliferation Reagent (Roche Applied Sciences, Indianapolis, Ind.) for the last three hours of the proliferation period.

The HER ligand polypeptide variants tested were: BiRegulin, BiRV35EG39L and EGF G39L wherein the B-loop domain was substituted with the corresponding domain from amphiregulin (G39L+Amp ds), EGF G39L wherein the B-loop domain was substituted with the corresponding domain from betacellulin (G39L+BTC ds); EGF G39L wherein the B-loop domain was substituted with the corresponding domain from epiregulin (G39L+Epi ds); and EGF G39L wherein the B-loop domain was substituted with the corresponding domain from TGF-alpha (G39L+TGF-alpha ds).

Figure 2:
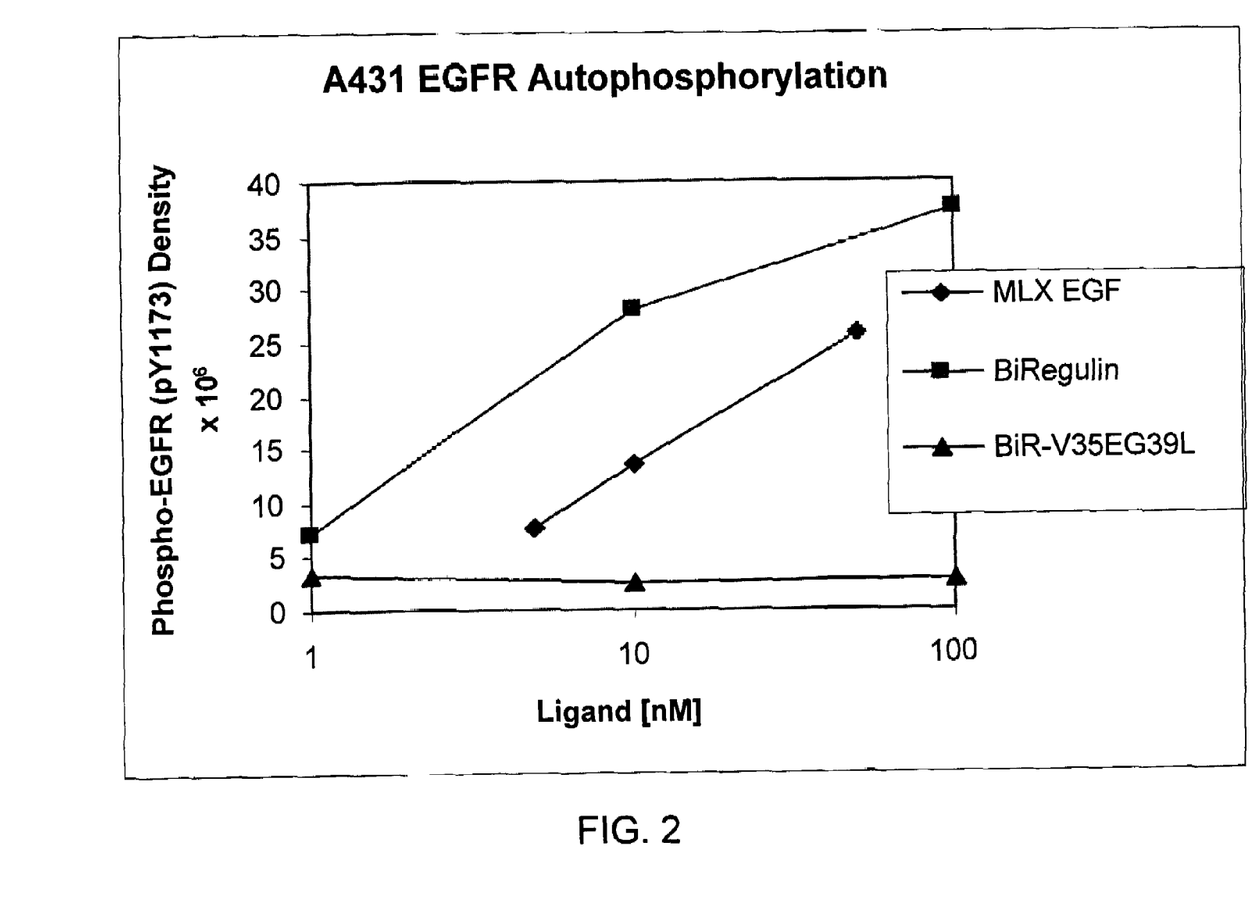
FIG. 2 is a graph depicting autophosphorylation of EGFR in A431 cells, an epithelial cancer cell line, stimulated by two agonistic ligands for EGFR, EGF and BiRegulin. BiRegulin with substitutions V35E and G39L does not stimulate autophosphorylation.
Figure 3:
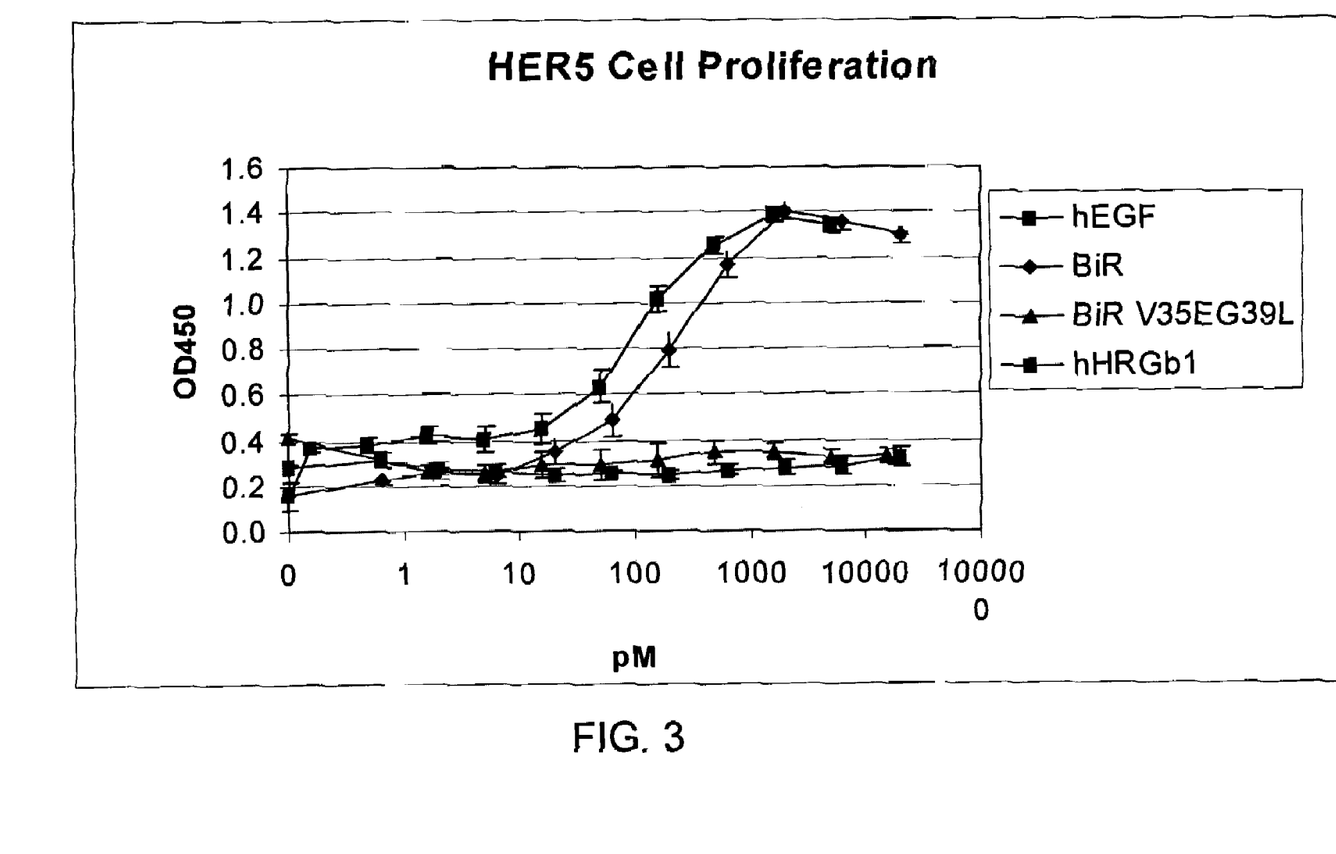
FIGS. 3 and 4 are graphs depicting stimulation of HER5 cells (mouse fibroblast cells that overexpress human EGFR) and MCF-7 cells (a human breast cancer cell line that express HER2 and HER3) respectively. HER5 cells can be stimulated by EGF and BiR but not by HRG. MCF-7 cells can be stimulated by BiR and HRG but not by EGF. Neither cell line is stimulated by BiRV35EG39L.

Autophosphorylation of EGFR in A431 cells, an epithelial cancer cell line, stimulated by two agonistic ligands for EGFR, EGF and BiRegulin is shown in FIG. 2. FIG. 3 also shows that BiRegulin with substitutions V35E and G39L does not stimulate autophosphorylation.

Figure 4:
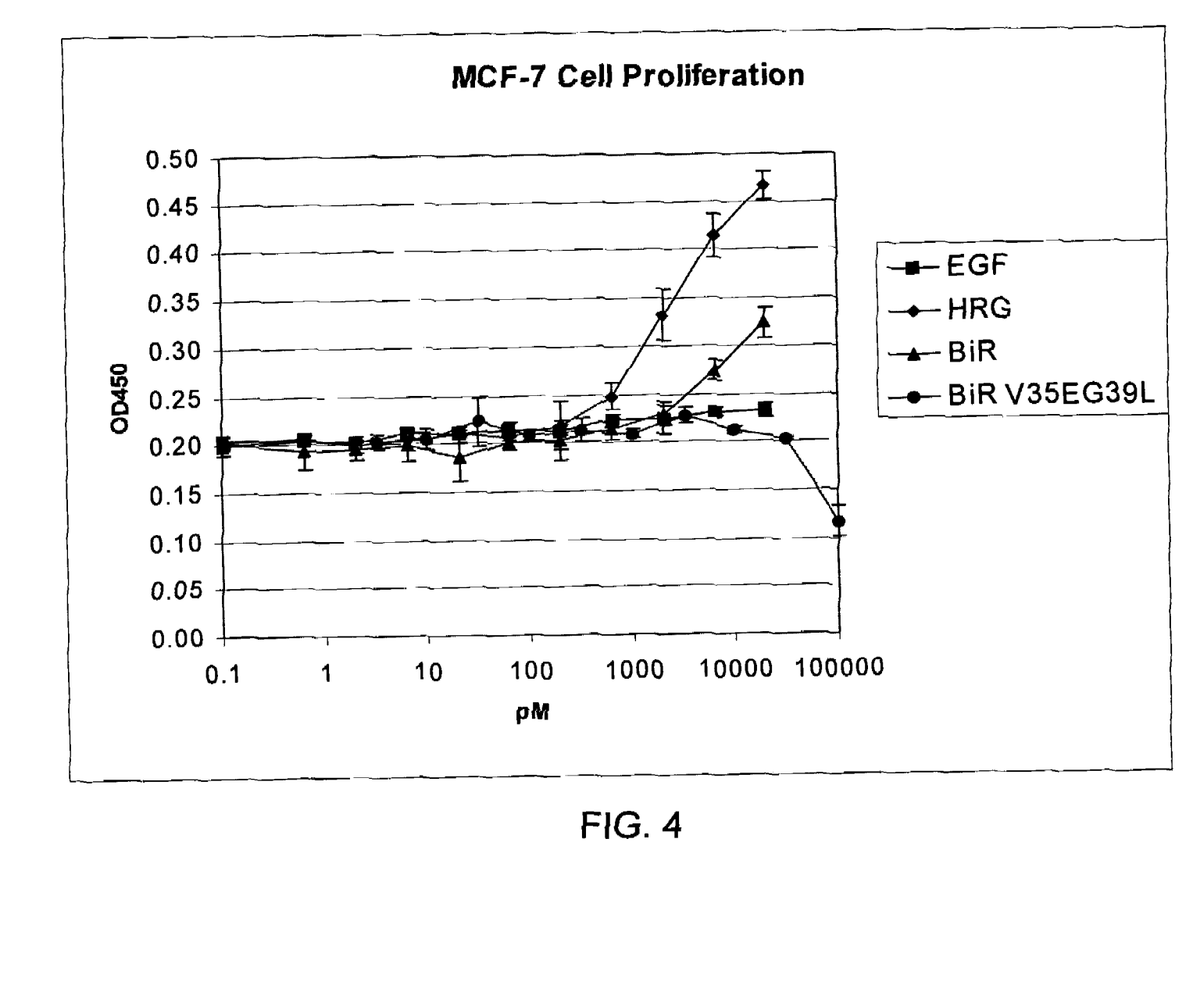
Figure 5A:
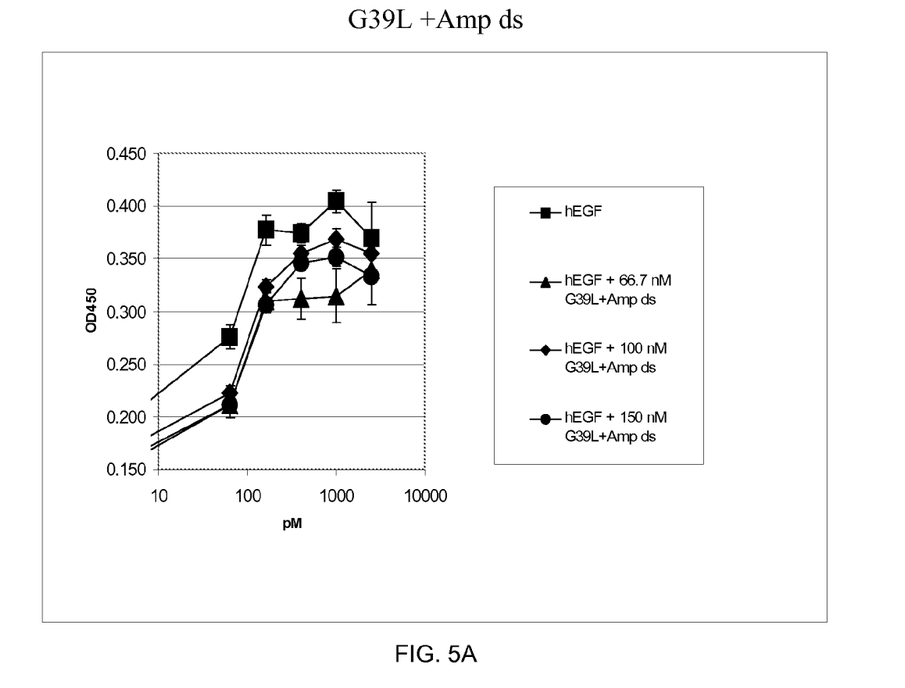
FIGS. 5A-5D are graphs depicting cell proliferation assays in the presence of the HER ligand polypeptide variants of the invention.
Figure 5B:
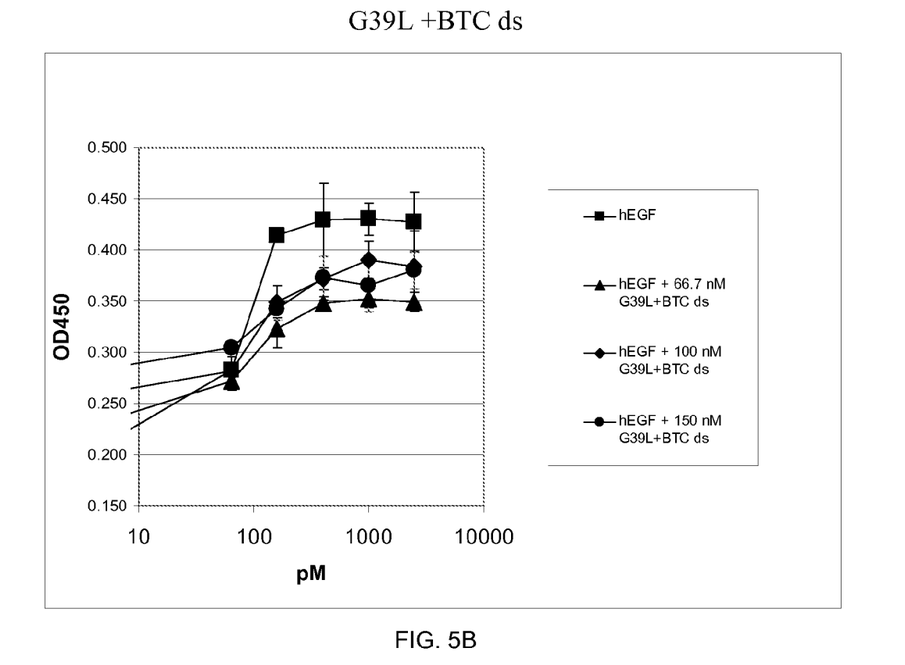
Figure 5C:
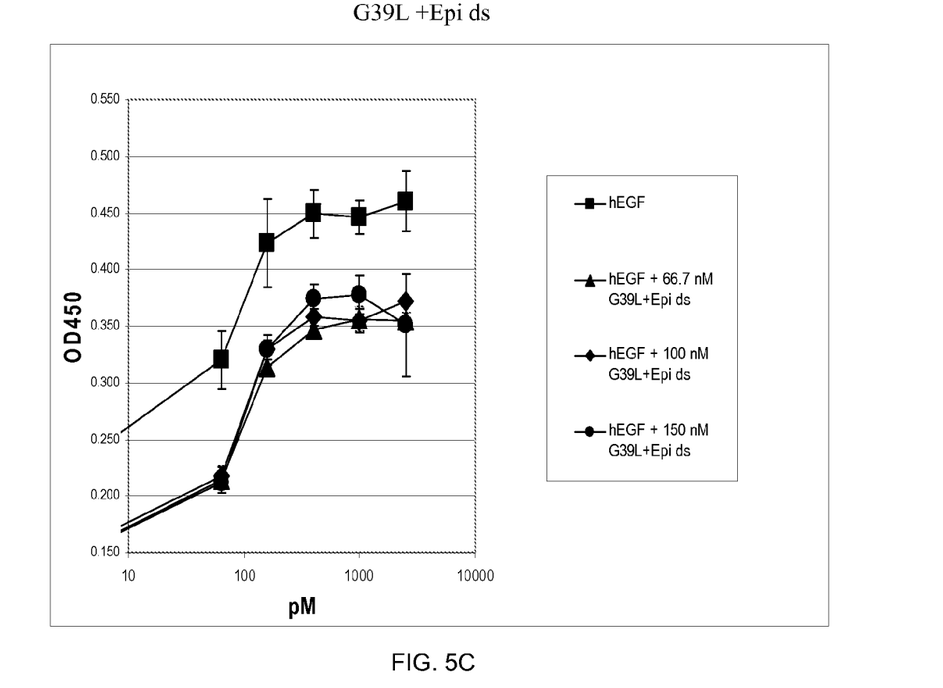
Figure 5D:
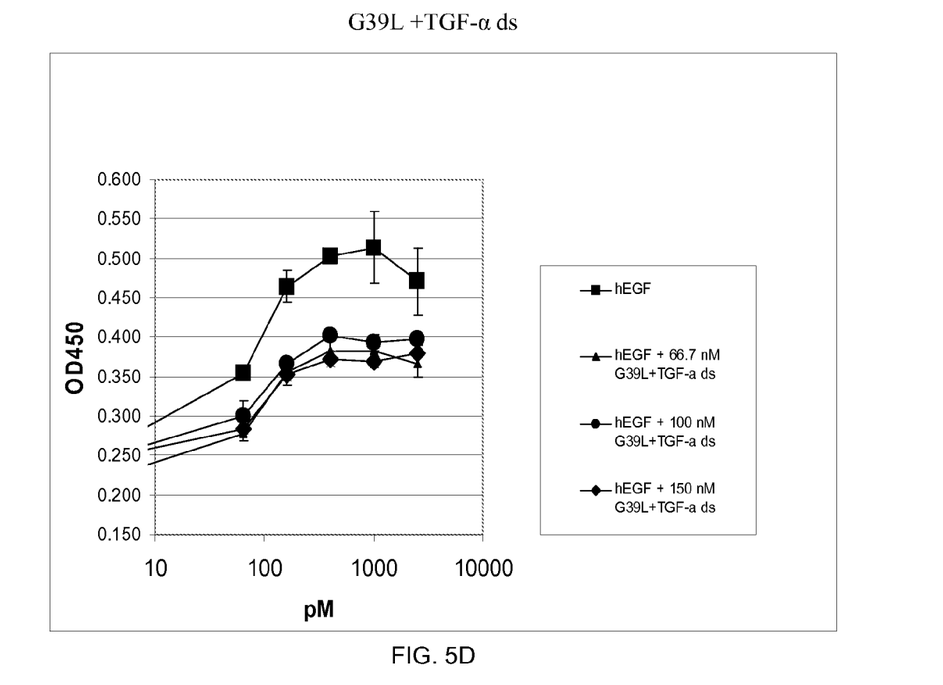

The stimulation of HER5 cells (mouse fibroblast cells that overexpress human EGFR) and MCF-7 cells (human breast cancer cell lines that express HER2 and HER3) are shown in FIGS. 3 and 4, respectively. HER5 cells can be stimulated by EGF and BiR but not by HRG. MCF-7 cells can be stimulated by BiR and HRG but not by EGF. Neither cell line is stimulated by BiRV35EG39L.

As shown in FIG. 5, the results indicate that domain swaps retain EGF G39L antagonist activity and continue to inhibit cell proliferation.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A human epidermal receptor (HER)-ligand polypeptide variant comprising a HER ligand polypeptide in which the amino acid position that corresponds to amino acid Gly 39 of human wild-type epidermal growth factor (EGF) is substituted with another amino acid, wherein the HER ligand polypeptide further comprises a substituted domain, and wherein the variant has at least one Pan-HER antagonist activity.

2. The variant of claim 1 wherein the HER ligand polypeptide is EGF.

3. The variant of claim 1, wherein the amino acid substitution is selected from the group consisting of: phenylalanine, leucine, aspartic acid, and isoleucine.

4. The variant of claim 1, wherein the amino acid substitution is leucine.

5. The variant of claim 1 wherein the substituted domain is the amino terminus of EGF.

6. The variant of claim 1 wherein the HER ligand polypeptide is EGF and the substituted domain is amino acids 1-5 of mature EGF corresponding to amino acids NSDSE (SEQ ID NO: 12).

7. The variant of claim 6 wherein the substituted domain of EGF is replaced with homologous amino acids of HRGβ1 corresponding to amino acids SHLVK (SEQ ID NO: 13).

8. The variant of claim 1 wherein the HER ligand polypeptide is BiRegulin (BiR).

9. The variant of claim 8 wherein amino acid Gly 39 is replaced with the amino acid, leucine.

10. The variant of claim 1 comprising at least one additional amino acid substitution at a position other than the amino acid position corresponding Gly 39 of wild-type human EGF.

11. The variant of claim 10, wherein the additional amino acid substitution is selected from at least one amino acid substitution at a position corresponding to G18, V35, and R41 of wild-type human EGF or any combination thereof.

12. The variant of claim 8 comprising an additional amino acid substitution at amino acid position V35.

13. The variant of claim 12 wherein the valine at amino acid position 35 is replaced with glutamic acid.

14. The variant of claim 13 comprising BiRV35EG39L.

15. The variant of claim 1, wherein the HER ligand polypeptide is selected from the group consisting of: human epidermal growth factor (EGF), transforming growth factor-α (TGFα), betacellulin, heparin-binding EGF-like growth factor (HB-EGF), neuregulins, heregulin, amphiregulin (AR) and epiregulin.

16. The variant of claim 1, wherein the substituted domain is the B-loop domain.

17. A HER ligand polypeptide variant of claim 1 comprising EGF G39L having a B-loop domain that has been substituted with a corresponding B-loop domain from another HER ligand polypeptide selected from the group consisting of: human epidermal growth factor (EGF), transforming growth factor-α (TGFα), betacellulin, heparin-binding EGF-like growth factor (HB-EGF), neuregulins, heregulin, amphiregulin (AR) and epiregulin, and wherein the variant has at least one Pan-HER antagonistic activity.

18. A composition comprising the HER ligand polypeptide variant of claim 1 and a pharmaceutically acceptable carrier.

19. A composition comprising the HER ligand polypeptide variant of claim 17 and a pharmaceutically acceptable carrier.

20. A human epidermal receptor (HER)-ligand polypeptide variant having at least one Pan-HER antagonist activity wherein the variant comprises a mutation that disrupts binding via Domain III and a mutation that enhances binding affinity via Domain I.

21. A variant of claim 20 further comprising a mutation that modifies receptor binding specificity.

22. A nucleic acid encoding the variant of claim 1.

23. A nucleic acid encoding the variant of claim 14.

24. A human epidermal receptor (HER)-ligand polypeptide variant having at least one Pan-HER antagonist activity wherein the variant comprises a mutation that disrupts binding via Domain I and a mutation that enhances binding via Domain III.

* * * * *

SEQUENCE LISTING

```
<160> NUMBER OF SEQ ID NOS: 11

<210> SEQ ID NO 1
<211> LENGTH: 53
<212> TYPE: PRT
<213> ORGANISM: Homo Sapien

<400> SEQUENCE: 1

Asn Ser Asp Ser Glu Cys Pro Leu Ser His Asp Gly Tyr Cys Leu His
 1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 53
<212> TYPE: PRT
<213> ORGANISM: Pig

<400> SEQUENCE: 2

Asn Ser Tyr Ser Glu Cys Pro Ser His Asp Gly Tyr Cys Leu His
 1               5                   10                  15

Gly Gly Val Cys Met Tyr Ile Glu Ala Val Asp Ser Tyr Ala Cys Asn
            20                  25                  30

Cys Val Phe Gly Tyr Val Gly Glu Arg Cys Gln His Arg Asp Leu Lys
        35                  40                  45

Trp Trp Glu Leu Arg
    50

<210> SEQ ID NO 3
<211> LENGTH: 52
<212> TYPE: PRT
<213> ORGANISM: Cat

<400> SEQUENCE: 3

Asn Ser Tyr Gln Glu Cys Pro Pro Ser Tyr Asp Gly Tyr Cys Leu Tyr
 1               5                   10                  15

Asn Gly Val Cys Met Tyr Ile Glu Ala Val Asp Arg Tyr Ala Cys Asn
            20                  25                  30

Cys Val Phe Gly Tyr Val Gly Glu Arg Cys Gln His Arg Asp Leu Lys
        35                  40                  45

Trp Glu Leu Arg
    50

<210> SEQ ID NO 4
<211> LENGTH: 52
```

```
<212> TYPE: PRT
<213> ORGANISM: Dog

<400> SEQUENCE: 4

Asn Gly Tyr Arg Glu Cys Pro Ser Ser Tyr Asp Gly Tyr Cys Leu Tyr
 1               5                  10                  15

Asn Gly Val Cys Met Tyr Ile Glu Ala Val Asp Arg Tyr Ala Cys Asn
            20                  25                  30

Cys Val Phe Gly Tyr Val Gly Glu Arg Cys Gln His Arg Asp Leu Lys
        35                  40                  45

Trp Glu Leu Arg
    50

<210> SEQ ID NO 5
<211> LENGTH: 53
<212> TYPE: PRT
<213> ORGANISM: Mouse

<400> SEQUENCE: 5

Asn Ser Tyr Pro Gly Cys Pro Ser Ser Tyr Asp Gly Tyr Cys Leu Asn
 1               5                  10                  15

Gly Gly Val Cys Met His Ile Glu Ser Leu Asp Ser Tyr Thr Cys Asn
            20                  25                  30

Cys Val Ile Gly Tyr Ser Gly Asp Arg Cys Gln Thr Arg Asp Leu Arg
        35                  40                  45

Trp Trp Glu Leu Arg
    50

<210> SEQ ID NO 6
<211> LENGTH: 48
<212> TYPE: PRT
<213> ORGANISM: Horse

<400> SEQUENCE: 6

Asn Ser Tyr Gln Glu Cys Ser Gln Ser Tyr Asp Gly Tyr Cys Leu His
 1               5                  10                  15

Gly Gly Lys Cys Val Tyr Leu Val Gln Val Asp Thr His Ala Cys Asn
            20                  25                  30

Cys Val Val Gly Tyr Val Gly Glu Arg Cys Gln His Gln Asp Leu Arg
        35                  40                  45

<210> SEQ ID NO 7
<211> LENGTH: 53
<212> TYPE: PRT
<213> ORGANISM: Rat

<400> SEQUENCE: 7

Asn Ser Asn Thr Gly Cys Pro Pro Ser Tyr Asp Gly Tyr Cys Leu Asn
 1               5                  10                  15

Gly Gly Val Cys Met Tyr Val Glu Ser Val Asp Arg Tyr Val Cys Asn
            20                  25                  30

Cys Val Ile Gly Tyr Ile Gly Glu Arg Cys Gln His Arg Asp Leu Arg
        35                  40                  45

Trp Trp Lys Leu Arg
    50

<210> SEQ ID NO 8
<211> LENGTH: 83
<212> TYPE: PRT
<213> ORGANISM: Artificial Sequence
```

```
<220> FEATURE:
<223> OTHER INFORMATION: Synthetic

<400> SEQUENCE: 8

Met Lys Lys Thr Ala Ile Ala Ile Ala Val Ala Leu Ala Gly Phe Ala
1               5                   10                  15

Thr Val Ala Gln Ala His His His His His Ile Glu Gly Arg Asn
            20                  25                  30

Ser Asp Ser Glu Cys Pro Leu Ser His Asp Gly Tyr Cys Leu His Asp
        35                  40                  45

Gly Val Cys Met Tyr Ile Glu Ala Leu Asp Lys Tyr Ala Cys Asn Cys
    50                  55                  60

Trp Gly Tyr Ile Gly Glu Arg Cys Gln Tyr Arg Asp Leu Lys Trp Trp
65                  70                  75                  80

Glu Leu Arg

<210> SEQ ID NO 9
<211> LENGTH: 53
<212> TYPE: PRT
<213> ORGANISM: Homo Sapien

<400> SEQUENCE: 9

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 10
<211> LENGTH: 53
<212> TYPE: PRT
<213> ORGANISM: Homo Sapien
<220> FEATURE:
<223> OTHER INFORMATION: Synthetic

<400> SEQUENCE: 10

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe
    50

<210> SEQ ID NO 11
<211> LENGTH: 53
<212> TYPE: PRT
<213> ORGANISM: Artificial Sequence
<220> FEATURE:
<223> OTHER INFORMATION: Synthetic

<400> SEQUENCE: 11

Ser His Leu Val Lys Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30
```

-continued

```
Cys Val Val Gly Tyr Ile Gly Glu Arg Cys Gln Tyr Arg Asp Leu Lys
        35                  40                  45

Trp Trp Glu Leu Arg
    50
```